United States Patent [19]

Löhn

[11] Patent Number: 4,504,227
[45] Date of Patent: Mar. 12, 1985

[54] DENTAL HANDPIECE SET
[75] Inventor: Gerd Löhn, Biberach, Fed. Rep. of Germany
[73] Assignee: Kaltenbach & Voight GmbH and Co., Biberach, Fed. Rep. of Germany
[21] Appl. No.: 477,216
[22] Filed: Mar. 21, 1983
[30] Foreign Application Priority Data Apr. 23, 1982 [DE] Fed. Rep. of Germany ....... 3215255

[51] Int. Cl.³ .................................................. A61C 1/06
[52] U.S. Cl. .................................... 433/131; 433/132; 433/126
[58] Field of Search ............... 433/126, 131, 132, 114, 433/105, 103, 29

[56] References Cited

U.S. PATENT DOCUMENTS

| 3,229,369 | 1/1966 | Hoffmeister et al. | 433/126 |
| 3,978,586 | 9/1976 | Etherington | 433/131 |
| 4,014,098 | 3/1977 | Scrivo | 433/29 |
| 4,306,865 | 12/1981 | Leonard | 433/105 |
| 4,348,180 | 9/1982 | Schuss | 433/126 |
| 4,353,697 | 9/1982 | Nakanishi | 433/126 |
| 4,382,790 | 5/1983 | Loge et al. | 433/126 |
| 4,403,958 | 9/1983 | Lohn | 433/126 |

FOREIGN PATENT DOCUMENTS

| 2422704 | 2/1974 | Fed. Rep. of Germany | 433/131 |
| 2810044 | 9/1979 | Fed. Rep. of Germany | 433/126 |

Primary Examiner—Robert Peshock
Assistant Examiner—John G. Weiss
Attorney, Agent, or Firm—Scully, Scott, Murphy & Presser

[57] ABSTRACT

There is disclosed a dental handpiece set which comprises a handpiece housing, a power supply module detachably coupled to one end of the housing for supplying power to operate the handpiece, a motor unit which is selected from a set of different types of motors and which is removably mounted in the housing as an exchangeable motor unit, and a drive train extending within the housing to an opposite end of the housing at which a dental implement can be mounted to be driven by the drive train when the motor unit is mounted in the housing and is coupled with the power supply module. The end of the housing which is detachably coupled with the power supply module is adapted removably to receive the selected motor unit so that a housing of the unit is secured within the housing against rotation. At least two different types of motor unit e.g. an air driven motor and an electric motor, are provided to be mounted selectively in the housing according to operating requirements for the handpiece, each motor unit being arranged so as to be capable of being received by the housing via said one end thereof and being adapted for coupling with the power supply module.

Accordingly, the dental handpiece set enables any desired combination of elements to be obtained to suit any available power supply module.

19 Claims, 8 Drawing Figures

DENTAL HANDPIECE SET

TECHNICAL FIELD OF THE INVENTION

This invention relates to a dental handpiece set comprising a handpiece housing, a power supply module detachably coupled to one end of the housing for supplying power to operate the handpiece, means provided in the housing to mount therein a motor unit which is coupled to the power supply module, and a drive train extending within the housing to an opposite end of the housing at which a dental implement can be mounted to be driven by the drive train when the motor unit is mounted in the housing.

BRIEF DESCRIPTION OF THE PRIOR ART

Dental handpiece apparatus of the above general type are known. In particular, there are two distinct types: air-driven handpiece apparatus (see U.S. Pat. Nos. 3,439,422 and 3,349,490) and electrically operated handpiece apparatus (see German Auslegeschrift No. 1 234 922). Common to both these types of design is the fact that the drive motor, in the one case a rotary vane type air motor and in the other case an electric motor, is integrally arranged i.e. permanently mounted in a handle casing or housing which is usually the same in both cases, and the shaft of the motor serves to drive a dental implement, such as a drilling tool. A coolant supplied via a supply component is conducted via an external line along the outside of the handle casing to the work area.

The disadvantage of the known constructions of handpiece is that the arrangement of individual components is always suitable only for one type of structure, i.e. in respect of power, rotational speed, torque, and is also intended for either a straight or an angled handpiece. Furthermore, the cooland lines are inconveniently positioned on the outside. Finally, the known handpieces are very long and therefore unwieldy in view of the necessary tilting moments which arise in a dentist3 s hand during normal operation.

The known dental handpieces are thus each designed for only one type of power supply, and for only one type of treatment. However, frequently different types of treatment are required, and also only incorrect power supplies may be available in any given environment to suit the particularly known apparatus.

It has already been proposed in respect of a handpiece operated by electric motor that a handle casing component in which a structural unit (consisting of a transmission and carrier which can be inserted axially and interchangeably) is provided for use with a drive component having the drive motor, and so that an angled or a straight head casing may be coupled as selected to this handle casing component (see German Auslegeschrift No. 2 810 044). This arrangement also is very long. Also, the arrangement cannot be used with drive components of a different construction.

Finally, it has been recognised that it is also advantageous with air-driven handpieces for the handle casing to be freely rotatable with respect to a supply hose. To overcome this problem a connecting piece which may be inserted into the handle casing was indicated (German Utility Model No. 77 29 110), which connecting piece has radially aligned outlet openings and to which the supply hose may be coupled at the front end, more particularly by means of a quick action coupling. This design too may only be used on particular handpiece apparatus, namely directly driven, air-operated handpiece apparatus.

Known types of construction of dental handpiece apparatus may therefore only be used on quite specific supply components, if appropriate on groups of quite specific supply components, which means, in particular, it is not possible for the same handpiece apparatus to be used as an air-operated or electrically operated handpiece. This means that, depending on the type of supply provided in each case and the type of drive desired in each case, a great many dental handpiece apparatus are required. As a result a dentist must, if need be, have several, and in some circumstances, a greater number of dental handpiece apparatus. This is obviously disadvantageous, especially as dental handpiece apparatus are expensive components. Therefore, a dentist seldom has the means to carry out treatment under optimum conditions.

It is therefore an object of the invention to design a dental handpiece set of the type described above so as to allow, with a compact construction, optimum treatment to be carried out at all times.

According to the invention there is provided a dental handpiece set comprising a handpiece housing, a power supply module detachably coupled to one end of the housing for supplying power to operate the handpiece, means provided in the housing to mount therein a motor unit which is coupled to the power supply module, and a drive train extending within the housing to an opposite end of the housing at which a dental implement can be mounted to be driven by the drive train when the motor unit is mounted in the housing:

in which said one end of the housing is adapted removably to receive the motor unit, as an exchangeable motor unit, so that a housing of the unit is securable against rotation within the handpiece housing;

and in which at least two different motor units are provided to be mounted selectively in the housing according to operation requirements for the handpiece, each motor unit being arranged so as to be capable of being received by the housing via said one end thereof and being adapted for coupling with the power supply module.

A dental handpiece set according to the invention enables the user to carry out optimum treatment, regardless of the type of power available at any given time, and also entirely irrespective of whether a power supply module is provided which is suitable for air-operated or electrically operated handpieces. Advantageously this allows components to be changed more quickly during work, and also allows an optimum assembly. Furthermore, it is possible for different assemblies of components of handpieces to be combined. Finally, as the individual components are interchangeable, the costs for replacement or new purchases are relatively low. Also, repairs are made much easier as it is necessary merely to repair the damaged part. In addition, the handpiece, in a preferred arrangement, is also suitable for the simple and integrated accommodation of coolant and signal lines, such as fibre optic cables. Furthermore, it is also possible to adapt the handpiece in a simple manner to another supply system, i.e. to a different power supply. For this, it is preferred to provide a new coupling adapter, suitable for the new power supply, into the handpiece housing.

DETAILED DESCRIPTION OF PREFERRED EMBODIMENTS OF THE INVENTION

Figure 1:
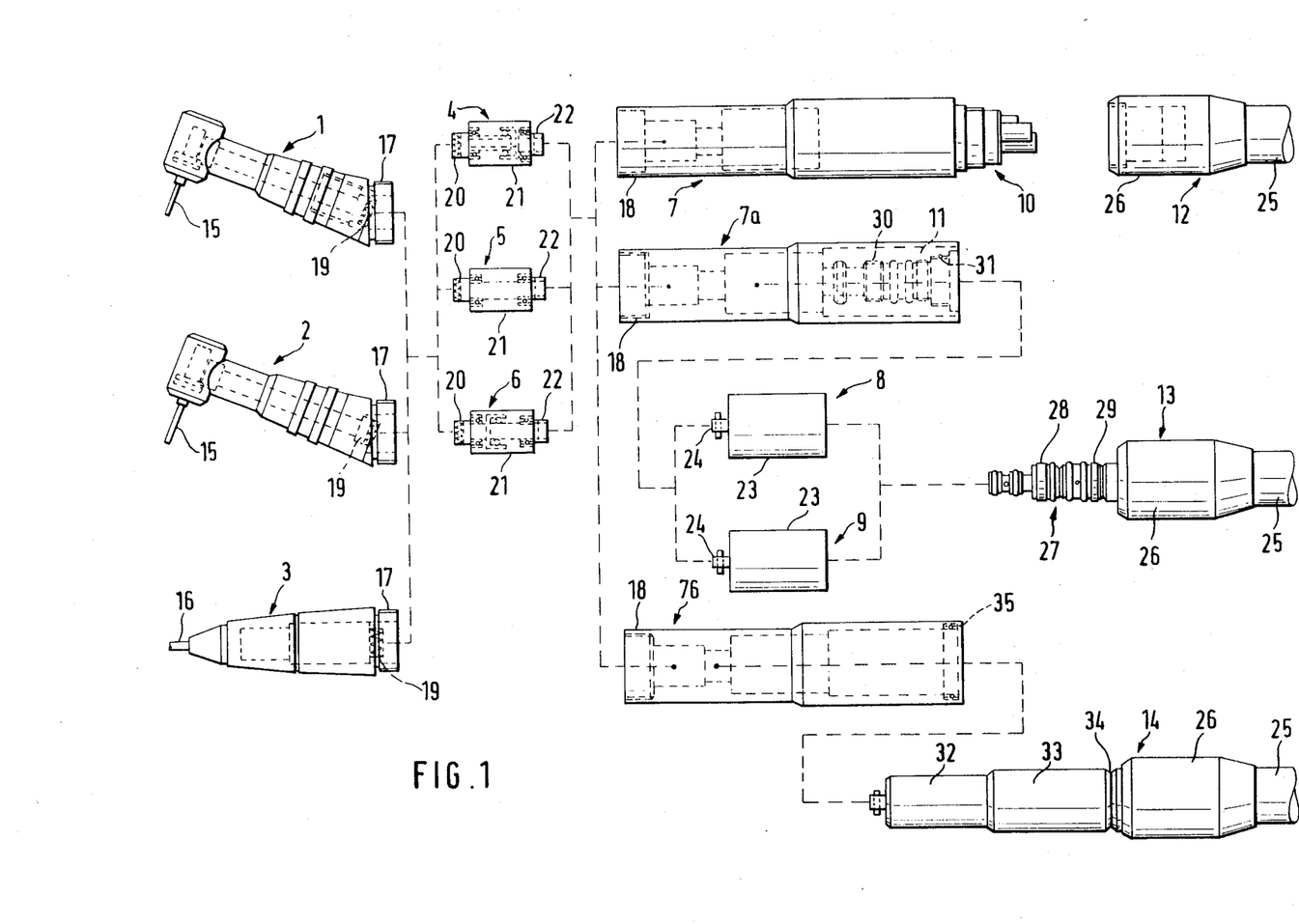
FIG. 1 shows diagrammatically the basic construction of a dental handpiece set according to the invention.

With reference to FIG. 1 the basic principle of the invention is firstly explained in more detail. FIG. 1 shows the different basic components of the dental handpiece set according to the invention, namely with reference to an exemplary embodiment of a handpiece housing with a transversely divided handle casing, namely tool-end handle casing components and drive-end handle casing components.

FIG. 1 shows firstly three different tool-end handle casing components 1,2 and 3, then, in addition, substantially identical drive-end handle casing components 7, 7a, 7b, two different motor units or cartridges 8 and 9, two different coupling adapters 10 and 11 in the inserted position in the drive-handle casing component 7 or 7a respectively and different power supply modules or components 12, 13 or 14 respectively.

The individual components can be interchangeably coupled together in the ways indicated by the dotted lines, so as to allow dental handpieces to be made up with different supplies, different step up or step down gear ratios and different tool-end treatment parts.

As shown diagrammatically, the tool-end handle casing component 1 is an angle piece handle casing component which incorporates near the coupling end at least one slipping clutch, and if necessary a further gear. Angle pieces of this type are known per se and are available commercially.

The tool-end handle casing component 2 has, as shown, an undivided, continuous drive shaft.

The two tool-end handle casing components 1 and 2 operate interchangeable dental implements, namely drilling tools 15.

The tool-end handle casing component 3 is designed for a so-called straight head casing and is used for example to drive a coaxial tool, for example a file 16 which has to reciprocate along the axis and if necessary also to rock about the axis. For this purpose, the tool-end handle casing component 3 includes a motion converting device which is not shown in detail.

Handle casing components of this type are common and known per se and for this reason are not described in more detail herein.

Another important factor of the present inventiion is that there are also several more tool-end handle casing components which can drive other tools to produce specific movements in each case and the handle casing components can be provided for angled head casings and for straight head casings.

At the end remote from the tool 15,16, the tool-end handle casing components 1,2,3 all have, on the one hand, a coupling element 17 for connection to a coupling element 18, which is clearly co-operating therewith, on the drive-handle casing component 7 or 7a, 7b respectively and also on the other hand a meshing part 19, such as radial serrations, on a drive shaft component for engaging with a correspondingly constructed meshing part 20 on the output shaft of a driving gear 4,5,6.

Each driving gear basically has a housing 21 which is essentially the same construction for all the driving gears 4,5,6, the output-end meshing part 20, and also a drive-end meshing part 22. The output-end meshing part 20 and drive-end meshing part 22 also have essentially the same construction for all the driving gears 4,5,6. The different driving gears 4,5,6 are distinguished by their internal construction, namely by the ratio between driving-end and output-end rotational speed. The driving gears 4 to 6 represented show the basic types, namely on the one hand a step up driving gear 4, on the other a direct equal speed driving gear 5 and finally a step down driving gear 6.

In addition, other driving gears are possible which have the same external construction as the driving gears 4 to 6, i.e. housing 21, output-end meshing part 20 and drive-end meshing part 22 but which have different gear ratios between the drive side and output side. Finally, as is known per se slipping clutches and other coupling elements may also be provided in the driving gears to prevent jolts or such like.

The drive-end handle casing component 7, for short the drive-handle casing component 7, of which there is at least one, is distinguished by the fact that on the one hand each driving gear 4,5,6 may be inserted so as to be secure against rotation from the end at which the drive-handle casing component 7 can be connected via its coupling element 18 to the tool-end handle casing component 1,2,3 via its coupling element 17. Thus, each driving gear 4,5,6 can be inserted into the drive-handle casing component 7 so that when the tool-end handle casing component 1,2 or 3 is coupled with the drive-handle casing component 7, its drive-end meshing part 19 is engaged with the output-end meshing part 20 of each driving gear 4,5 or 6 respectively. The drive-end meshing part 22 of each driving gear 4,5,6 is set into motion—i.e. rotated, in the drive-handle casing component 7 by a further drive device described below.

Dental tools are essentially divided into those operated by a fluid, namely more particularly air, and those operated by electric current. It is possible to use both basic drive possibilities in a dental handpiece set according to the invention. For this purpose at least two different motor units 8 and 9 are provided, one of which is a fluid motor, more particularly an air motor 8, and the other an electric motor 9. As shown and as will be explained in more detail, both motor units have an essentially identical housing 23 and an output-end meshing part 24. The output-end meshing part 24 of each motor unit 8,9 is designed so that it may be rotationally engaged with the drive-end meshing part 22 of each driving gear 4,5,6. This means that the air motor 8 and the electric motor 9 operate in each case on an output shaft having ends projecting outside the motor unit which are essentially designed to form the meshing part 24. The drive-handle casing components 7 and 7a, 7b respectively are further constructed so that each motor unit 8,9 may be introduced from the other end so that, when inserted, it may come into rotational contact via the output-end meshing part 24 with the drive-end meshing part 22 of the driving gears 4,5,6 (when they are inserted in the drive-handle casing component).

This allows the tool 15 and 16 respectively to be operated as required and with the required rotational speed or velocity, irrespective of which supply system is available. This means that it may be sufficient to have only one drive-handle casing component 7, whether the available power supply is a fluid supply or electric current supply.

In order now to be able to supply the power produced by the respective supply to the motor unit 8,9 which is suitable for the supply, a coupling adapter 10 and 11 respectively is advantageously provided which is designed to receive the different types of power supply components 12, 13.

The supply component 12 is constructed as a socket component, while the supply component 13 is constructed as a plug component.

The supply component 12 basically has a hose 25 which contains all the necessary (and usual) supply lines, such as lines for compressed air, cooling fluid, etc. At the end of the hose 25 facing the drive-handle casing component 7, the supply component 12 has a sealing part 26, which has not been shown in detail and which has externally a screw-threaded union, by means of which the supply component 12 can be coupled to the handle casing component 7. In an advantageous embodiment the sealing part 26 and the drive-handle casing component 7 are not meshed by means of a screw-threaded engagement, but by means of a quick action coupling mechanism, such as a bayonet engagement or similar.

In the case of the supply component 13, a projecting spigot 27 containing fluid outlets next to each other in the axial direction and separated by seals, is added to the front end of the hose 25. In the embodiment shown this projecting spigot 27 has in addition electrical annular contacts 28 and 29 respectively so as to make it possible for the supply to be both a fluid supply and an electric current supply so that, as indicated diagrmmatically in FIG. 1, this supply component 13 is capable of driving both an air motor 8 and also an electric motor 9.

The drive-handle casing component 7a shows inside a coupling adapter 11 which is designed for coupling with the spigot 27 of the supply component 13 such that the spigot 27 and the drive-handle casing component 7a may be mutually rotated as required, and in any of the optional rotational positions the fluid and the electric current can be collected in a suitable manner and supplied to the corresponding motor unit 8 and 9 respectively. This happens in a way which is common per se and is explained in more detail for the supply of fluid. For supplying the electric motor 9 the electric current is picked up via the electrical annular contacts 28,29 by means of slip rings 30 and 31 respectively in the coupling adapter 11. The spigot 27 is designed to snap into the coupling adapter 11 such that, when snapped in, a secure connection is made between the supply component 13 and the handle casing component 7a which can, however, be released by pulling.

In the supply component 12 according to FIG. 1 the coupling adapter 10 is of a different construction. It is in fact designed so that its end projecting from the handle casing component 7 can engage with the corresponding fluid lines at the front end of the hose 25 of the supply component 12 when the supply component 12 is connected via the sealing part 26 with the handle casing component 7.

As is known per se (cf. German Utility Model No. 77 29 110) the coupling adapter 10 can be in two parts, one part substantially corresponding to the coupling adapter 11 and being arranged inside the handle casing component 7 and the other, externally projecting part being connectable in the aforementioned way with the supply component 12. In this connection this externally projecting part of the coupling adapter 10 is rotatable as required in the part inserted inside the handle casing component 7, this being achieved by a connection like that described above between the spigot 27 of the supply component 13 and the coupling adapter 11 for the handle casing component 10. The coupling adapter 10 may also, however, be constructed in one piece.

What is important is that the coupling adapter should be designed on the one hand for supplying the motor unit 8 and/or 9, while being designed on the other for the coupled connection with a supply component. By an appropriate choice of coupling adapter, any type of supply component can be used for driving the tools 15, 16, using a specific motor unit 8,9 in each case.

The only occasion when the end facing the supply component should be of corresponding design, i.e. when several types of handle casing components 7, 7a might be required, is when different types of sealing parts 26 are provided for connection with the handle casing components 7, 7a respectively.

The power supply component 14 of the embodiment of the invention according to FIG. 1 differs from the power supply components 12 and 13 essentially by the fact that it contains the motor unit as a built-in or integrated motor cartridge 32 and here too the output-end meshing part as meshing part 24 is constructed in the same way as in the motor units 8 and 9. The power supply component 14 has as a transition piece between its motor cartridge 32 and the sealing part 26 and the hose 25 respectively a transition piece 33 to equalize the length, and this transition piece 33 merely has to be inserted into the drive-handle casing component 7 and 7a, 7b respectively. However, the supply component 14 must be inserted into the handle casing component securely but detachably, for which purpose the transition piece 33 contains in the embodiment shown an annular groove 34 into which latching elements 35 in the handle casing component 7b can be snapped to secure this. These latching elements 35 may, as shown for the handle casing component 7b, be provided integrally in this. Although not shown in detail, the latching elements 35 may, however, form a coupling adapter which may be interchangeably inserted into a drive-handle casing component of common construction.

What is essential for the invention is that it should be possible to use any power supply component for operating any tool with the minimum number of components to prepare. As has been explained, it may be sufficient to provide a single drive-handle casing component 7a into which coupling adapters appropriate for each supply component used can be inserted so that a motor unit 8 or 9 can be supplied as selected.

The aforementioned embodiment, also having interchangeable driving gears and interchangeable tool-end handle casing components, is of particular advantage in this connection. However, it may be sufficient to provide handle casings which have a driven and a tool-end handle casing component integrally connected with the drive-handle casing component. In this embodiment the motor unit 8 or 9 can only be interchangeably inserted, while the transmission and the tool operated and also the manner of operating the tool are no longer freely selectable. For this reason it is advantageous if the driving gears and tool-end handle casing components are also interchangeable.

Figure 2:
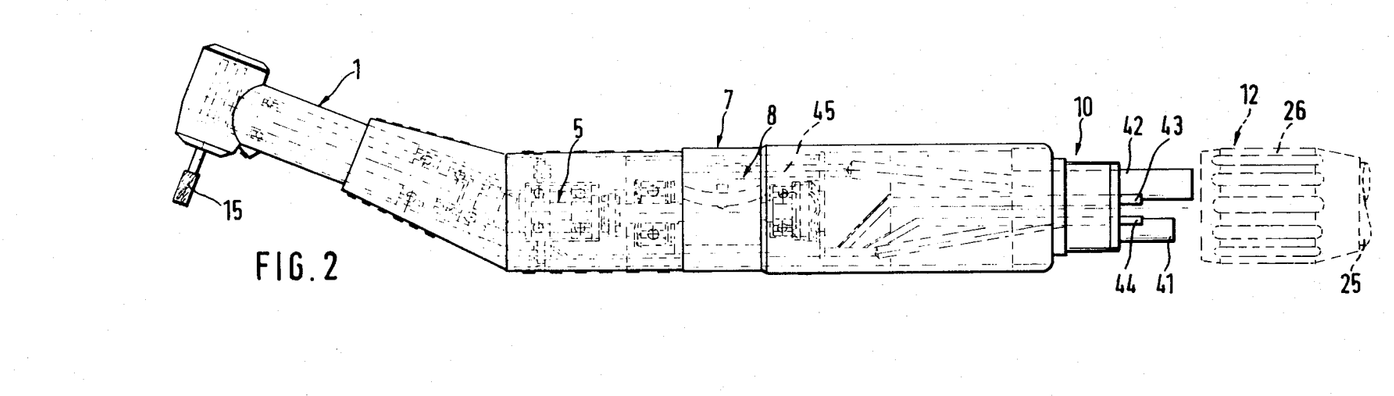
FIG. 2 shows diagrammatically the constructional details of a first embodiment of the invention.
Figure 3:
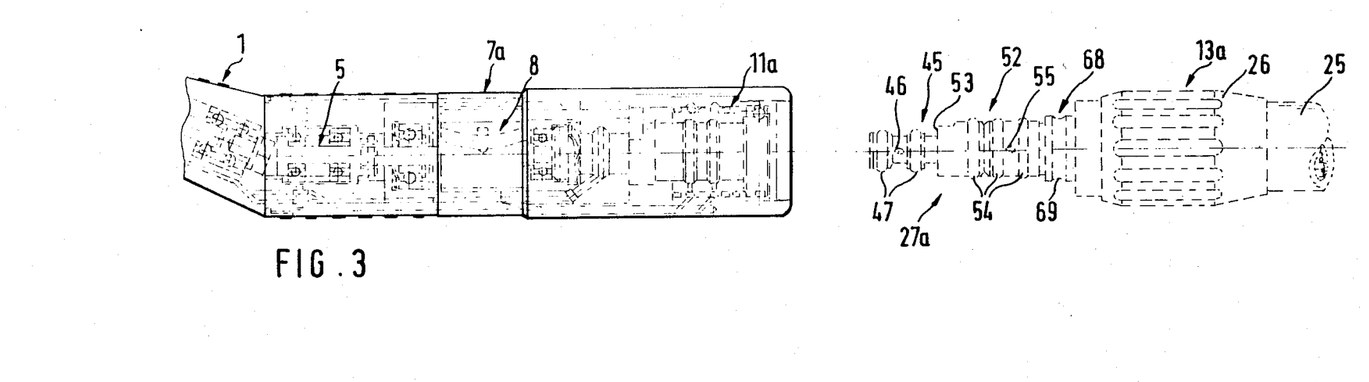
FIG. 3 shows diagrammatically a second embodiment of the invention.

An embodiment of the invention is explained in more detail in the following with reference to air-operated dental handpieces, i.e. with reference to handpieces which contain an air motor 8 as the motor unit or cartridge. FIG. 2 shows an embodiment in which the power supply component 12 acts via a coupling adapter 10 directly on the air motor 8 in the handle casing component 7. FIG. 3 shows an exemplary embodiment in which a supply component 13a, which is distinguished from the supply component 13 according to FIG. 1 by the fact that there are no electrical contacts 28,29, acts via a corresponding coupling adapter 11a on the air motor 8 in the handle casing component 7a.

Both the exemplary embodiments according to FIG. 2 and according to FIG. 3 have in common the fact that the air motor 8 acts via a driving gear 5 on a tool-end handle casing component 1 and thus drives the tool 15 fitted therein. The air motor 8 in question is, as shown diagrammatically in FIGS. 2 and 3 and as will be explained in more detail with reference to FIGS. 4 to 8, a vaned air motor which operates on a principle known per se. The exemplary embodiments according to FIGS. 2 and 3 are thus distinguished essentially by the design of the respective coupling adapter 10 and 11a respectively for the connection to the respective supply component 12 and 13a, to produce rotation of the air motor 8 and thus to drive the tool 15. FIGS. 2 and 3 also show that it is not only the air driving the air motor 8 which may be supplied via the supply component 12 and 13a respectively, but that also other media such as cooling fluid and signals, for instance electrical or light signals or also illumination power, which may be supplied via the power supply component 12 and 13a respectively and conducted as far as the work region. It should also be noted that the motor unit 8 and also the motor unit 9 may be designed so as to enable the motor unit to be cooled by means of the cooling fluid supplied, as is known per se (cf. German Patent Specification No. 12 34 922).

The coupling adapter 10 according to FIG. 2 thus has an air supply line 41, an air outlet line 42, a cooling liquid line 43 and a cooling air line 44 which, on the end facing the supply component 12, project out from the coupling adapter 10 to form a connection piece and may be engaged with corresponding meshing parts (not shown) in the supply component 12. The coupling adapter 10 guides the lines 41 to 44 inside so that at the other end facing the air motor 8 they emerge at quite specific, defined positions. These positions correspond to the positions of corresponding connecting lines in the air motor 8, such as for example a connecting line 45 for connection with the air outlet line 42. In this connection there is a definite coupling, for example via meshing members, between the coupling adapter 10 and the air motor 8 so that the fluid in question can be conducted without any loss via the coupling adapter 10 to the air motor 8. At the end of the air motor 7 remote from the coupling adapter 10 there are suitable transition points for the cooling liquid line into the handle casing component 7, and also from this in turn into the tool-end handle casing component 1 such that, when they are fitted together, it is possible for the cooling liquid to be safely supplied via the cooling liquid line 43 and for the cooling air to be safely supplied via the cooling air line 44 to the work region. This will be explained below again in more detail. It is therefore essential that both the air motor 8 and also the coupling adapter 10 can be inserted into the handle casing component 7 in a defined position and so as to be secure against rotation, so that the respective lines, mutually sealed, can also be joined together in an aligned flow connection. Similar measures can be taken if a signal line (electric current) and/or a light line, such as through a glass fibre optic cable or similar, are provided.

A snap connection for the coupling adapter 10 in the handle casing component 7 is advantageous but not absolutely necessary as it is also possible for it to be secured by means of the screw-threaded nut of the supply component 12.

Figures 4, 5:
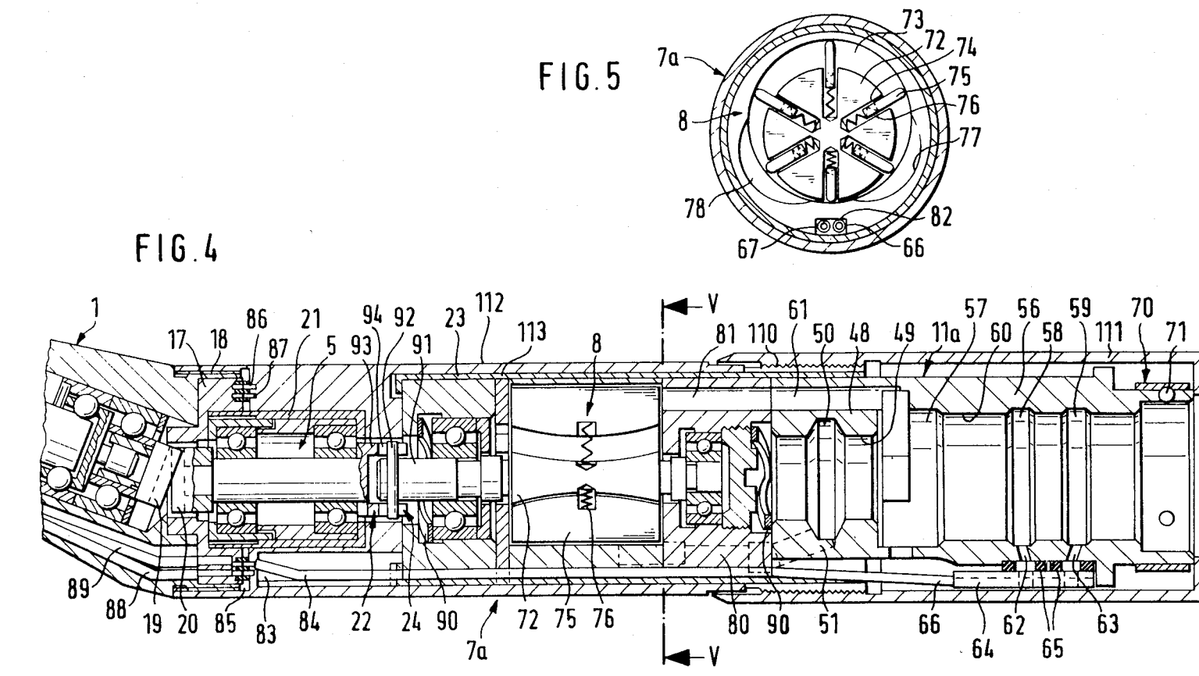
FIG. 4 shows in section details of the embodiment according to FIG. 3.
FIG. 5 is a section alone line V—V in FIG. 4.

The exemplary embodiment according to FIG. 3 shows an embodiment in which the air supply and air outlet, and also the supply of cooling liquid and cooling air are effected in a different way. As already mentioned the supply component 13a has a projecting spigot 27a which has the outlet openings for the various media. The coupling adapter 11a is then constructed in a corresponding way. Details of the coupling adapter 11a are shown in FIG. 4. At the front end the projecting spigot 27a has a section 45 of smaller diameter which contains a radial opening 46 for supplying the air. On both sides of this opening 46 annular seals 47 or O rings are mounted on the section 45. In a complementary manner the coupling adapter 11a has on its front end, i.e. on its end facing the air motor 8, a section 48 with an inner bore 49 of smaller diameter. An annular groove 50 is provided approximately centrally in the inner bore 49. The annular groove has a connection 51 for the corresponding connection to the air motor 7, which has yet to be explained.

When the supply component 13a (cf. also FIG. 6) has been inserted into the coupling adapter 11a, the opening 46 is in alignment with the annular groove 50 and the annular seals 47 externally seal the space of the annular groove by contact with the inner bore 49 on both sides of the annular groove 50. The supply air may then be supplied via the connection 51 to the air motor 8 in order to drive this.

A central section 52 of the spigot 27a has at the front side, i.e. on the annular surface 53 facing the front section 45, an opening (not shown) for air discharge. This air outlet opening may also be provided on the adjoining cylinder section. Adjoining this three annular seals 54 or O rings are mounted on the central section 52, separating the regions of the section 52 in which openings for the cooling liquid and the cooling air are provided, of which only one opening 55 is shown.

In a complementary manner the coupling adapter 11a also has a central section 56 which at its end facing the front section 48 has a radial enlargement 57 and which has in its length two annular grooves 58 and 59. The diameter of the enlargement 57 and of the annular grooves 58 and 59 is greater than the internal diameter of the inner bore 60 of the central section 56. When the spigot 27a of the supply component 13a has been inserted into the coupling adapter 11a, the annular seals 54 separate the enlargement 57 from the annular grooves 58 and 50 in a sealed manner and also separate the two annular grooves 58 and 59 from each other in a sealed manner by bearing on the inner bore 60 on both sides of the annular grooves 58 and 59 in each case.

The enlargement 57 is connected via a connection 61 with a corresponding, yet to be explained outlet line of the air motor 8. In a similar way, the annular grooves 58 and 59 are connected via connections 62 and 63 respectively with line connections, only one of which, namely the line connection 64, has been shown. The transition between the connections 62 and 63 and the respective line connection 64 is made in a sealed manner with the aid of seals 64. Adjoining each respective line connection 64 is a pipe connection 66 and 67 respectively which allows cooling air or cooling liquid to be connected and thus supplied to the work area, as will be explained.

Next to the central section 52, the spigot 27a has another rear section 68 of greater diameter which has an annular groove 69. The coupling adapter 11a has a rear section 70 complementary to this which has spaced around its periphery latching members 71 which are designed for locking in the annular groove 69 of the spigot 27a.

When inserted into the coupling adapter 11a, the supply component 13a is held in the coupling adapter 11a by the latching members 71 locking in the annular groove 69. In any rotational position of the supply component 13a it is possible for the other components to be supplied with supply air, cooling liquid, cooling air and also for these to be discharged (cf. also FIG. 6).

In a way known per se the air motor 8 is constructed as a vaned air motor. It has (cf. more particularly FIG. 5 and FIG. 7) a central shaft 72 which is rotatable as an eccentric in a circular chamber 73. The shaft 72 has radial slots 74 in which vanes are pressed radially outwards by the action of the force of a spring 76, to bear on the inner wall of the chamber 73. Slightly offset from the point where the shaft 72 is closest to the inner wall of the chamber 73, air is supplied which acts on the vanes and rotates these together with the shaft 72, and the supplied air leaves the inner chamber 73 where there is the greatest distance between the shaft 72 and inner wall of the inner chamber 73. Depending on which side of the closest point the air is supplied, the shaft 73 turns to the left or right. The air motor 8 is constructed in a way known per se so that air can be supplied to the inner chamber 73 both to the right and to the left of the closest point, so that the supply takes place as selected either to the right or the left. For this purpose the air motor 8 has a first supply opening 77 and a second supply opening 78, the opening 77 represented in FIG. 5 being provided for anticlockwise rotation and the opening 78 for clockwise rotation. According to the angle of the coupling adapter 11a to the air motor 8, either the opening 77 or the opening 78 will co-operate via the connection 51 in the coupling adapter 11a and with a connection 79 and 80 respectively aligned therewith in each case (cf. also FIG. 8), one being in connection with the first opening 77 and the other with the other opening 79. The inner chamber 73 is connected at its end having the greatest width via a connection 81 with the connection 61 in the coupling adapter 11a whatever the respective angular position so as always to ensure that air can be discharged from the inner chamber 73.

In addition the air motor 8 has (in the same way as a corresponding electric motor 9) a passage 82 for the cooling media lines 66 and 67. As the supply of cooling media should be independent of the angular position of the coupling adapter 11a and thus of the direction of rotation of the motor, the line connections 66 and 67 (in the passage 82) between the line connections 64 on the coupling adapter 11a and corresponding coolant line sections 83 and 84 passages 82 are designed so that the supply is safely guaranteed whatever the angle of the intermediate piece 11a.

Furthermore, it is necessary to ensure a secure connection of these coolant lines 83,84 via the front end of the drive handle casing component 8a to the tool-end handle casing component 1. For this purpose annular grooves 86 and 87 respectively are provided in a front end wall 85 of the drive-handle casing component 8a and they ensure a connection with the line sections 83,84 in the handle casing component 72 and corresponding line sections 88 and 89 respectively in the tool-end handle casing component 1 when this is securely connected to the drive-handle casing component 7a. This is advantageously achieved by a sealed bearing of the annular grooves 86,87 against corresponding annular grooves in the coupling element 17 which are in connection with the line sections 88 and 89, respectively. It has thus proved to be advantageous if the line sections 83,84 and the line sections 66,67 and also the respective line connection 64 are constructed in one piece and are provided in a fixed manner in the handle casing component 7a such that the respective motor unit 8,9 is placed by means of its passage or recess 82 over these lines. However, this is not essential. What is important, however, is that there can be a secure connection between the individual media supply lines.

The shaft 72 of the air motor 8 is mounted in a way known per se in the housing 23 and is axially supported by spring washers 90 so as thus to be better able to accommodate tolerances in the axial dimensions.

The meshing part 24 is provided at the end facing the respective drive gear and is constructed in the same way for both the motor units 8,9. In the exemplary embodiment shown the meshing part 24 of the motor units 8,9 consists of a transverse coupling pin 92 diametrically crossing the shaft end 91, while the corresponding meshing part 22 of each driving gear 4,5,6 consists of a shaft extension 93 with diametrical slot 94. The transverse coupling pin 92 can be inserted in this slot 94 and thus makes the shaft extension 93 of the driving gear rotatable.

FIG. 4 shows an exemplary embodiment in which the driving gear 5 is used with equal speeds i.e. 1:1 transmission. This means that the shaft extension 93 is positioned on a continuous shaft fixed in the housing 21 of the driving gear 5 on the other end of which is the meshing part 20 which is rotated with the same rotational speed as the shaft extension 93. The meshing part 20 is constructed as a radial serration and thus allows engagement in a correspondingly constructed meshing part 19 of a tool-end handle casing part 1,2 or 3. A drive engagement is thus achieved both with an angled and also with a straight tool-end handle casing component. The handle casing component 1 represented in FIG. 4 also shows a drive unit which is familiar per se and is thus not explained in more detail, and which acts on the meshing part 19.

As mentioned above it is possible for there to be a connection following the same principle of a supply component with electrical lines, for example via slip rings 28,29 (cf. FIG. 1).

Furthermore, in the same way as for the coolant lines 66,67 it is possible for signal lines to be provided to transmit for example electrical or optical signals to the work region, or from this to the supply component.

Figures 6, 7, 8:
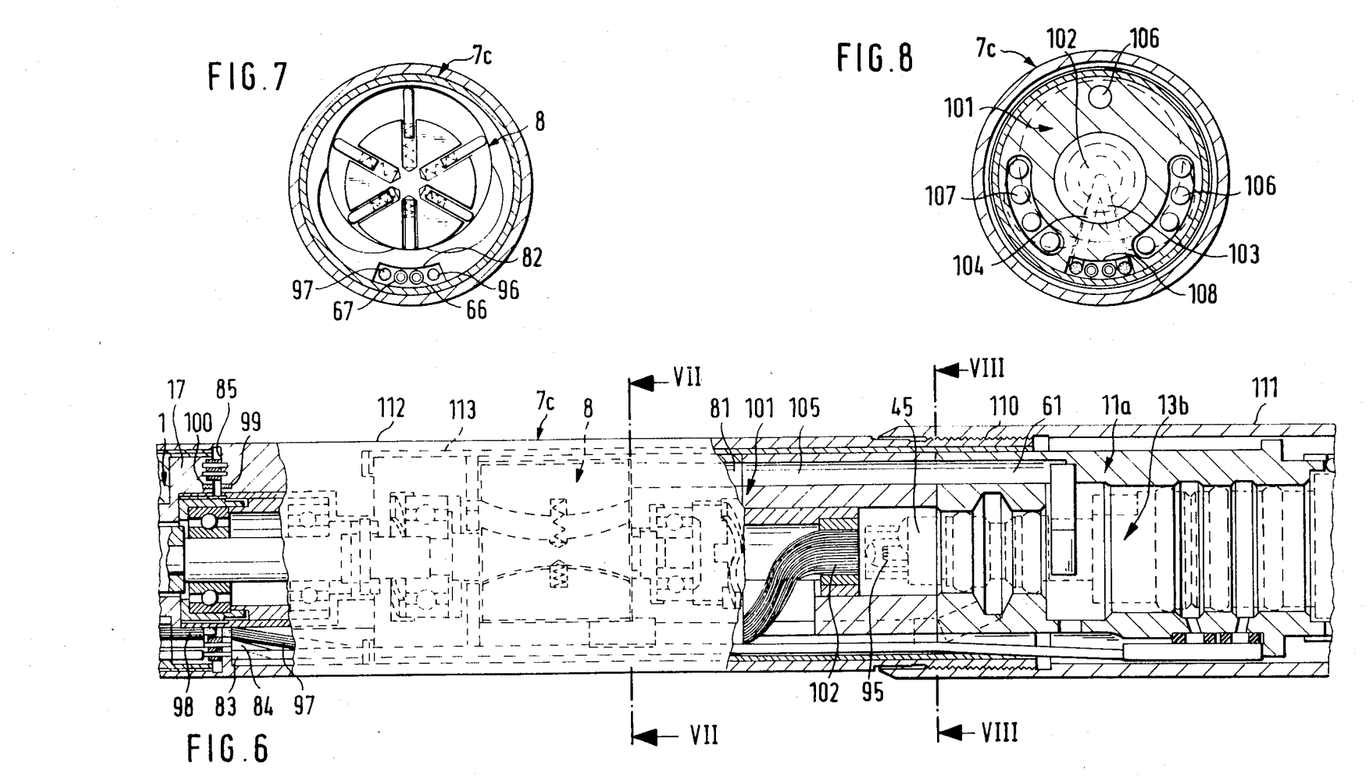
FIG. 6 shows in section, corresponding to FIG. 4, a further embodiment of the invention.
FIG. 7 is a section along line VII—VII in FIG. 6.
FIG. 8 is a section along line VIII—VIII in FIG. 6.

FIGS. 6 to 8 show a special embodiment in which light signals can be conducted from the power supply component to the work region.

In this embodiment, there is a power supply component 13b which corresponds in all essential details to that of power supply component 13a of FIG. 3 and thus to that which may also be used with the exemplary embodiment according to FIGS. 4 and 5. It may thus be inserted into a coupling adapter 11a, as has already been explained.

However, the supply component 13b differs from the supply component 13a by the fact that a light-emitting device is provided on the front end of the section 45. In the exemplary embodiment represented this is a lamp 95. It may also be a light emitting diode (LED) or a similar device. If appropriate, this light emitting device may also be the front end of a fibre optic light guide. As, however, the motor units take up a considerable and essentially central area, the light signals must be conducted past the motor units 8,9 in a similar way as the coolant lines 66,67 and 83,84 respectively. This means that, as shown in FIG. 7, not only are the lines 66 and 67 provided in the recess 82, but also corresponding light-transmitting conductors, namely fibre optic light guides 96 and 97. In the same way as for the coolants, the light signals are supplied from the fibre optic light guides 96, 97 to corresponding fibre optic light guides 98 in the tool-end handle casing component 1 via light transmitting members, such as fibre optic wave guides set in annular grooves 99 and 100 respectively which are provided in the end wall 85 and in the coupling element 17 respectively and are positioned opposite each other.

It is also essential for the light signals to be transmitted from the approximately axially provided lamp 95 to the fibre optic light guides 96 and 97 which are provided on the outer edge of the handle casing component 7c.

This may be effected in the same way as that explained for the fluid lines and for the slip ring connections for electrical contacts. However, the examplary embodiment shown is advantageous. In this embodiment an intermediate part 101 is additionally provided which is inserted between the motor unit 8 used and the coupling adapter 11a used into the drive-handle casing component 7c. In the middle the intermediate part 101 has a fibre optic light guide 102 which is directly opposite and a short distance away from the lamp 95 when the power supply component 13b has been inserted into the coupling adapter 11a, and which is divided in the represented exemplary embodiment into two strands 103 and 104 (cf. FIG. 8) which merge externally into the fibre optic light guide 96 and 97 respectively in the recess 92 of the air motor, for example via corresponding coupling pieces (not shown). Obviously, it is also possible for other signal lines to merge in a corresponding manner.

In addition it is essential that corresponding connections 105 should be provided in the intermediate part 101 between the connections 61 and 81, and 106 and 107 respectively between the connection 51 and the openings 77 and 78 respectively. Also, a recess 108 is of course provided which has the same function as the recess 82 in the motor cartridge 8 and 9 respectively, i.e. to receive the coolant lines and/or signal lines.

It is clear therefore that the drive-handle casing component 8c of this exemplary embodiment must have different dimensions in the axial direction than the handle casing component 8a of the previously described exemplary embodiment in order to be able to accommodate additionally the intermediate part 101.

The drive-handle casing component therefore advantageously consists of two components 111 and 112 connectable together via a screw thread 110.

In this connection it is advantageous for the drive-end component 112 of the handle casing component 7c to be designed to receive the respective motor unit 8,9 of the intermediate component 101 and of the respective driving gear 4 to 6, while the rear component 111 of the handle casing component 7c facing the respective supply component is designed to receive the respective corresponding coupling adapter 10,11,11a, and if necessary also latching elements 35.

In this connection, the tool-end component 112 is advantageously designed to receive a socket 113 receiving both the motor unit 8,9 and also the intermediate piece 101. The socket 113 preferably has the guide means required for inserting the coupling adapter in the correct position.

Finally, it should also be mentioned that the individual components are preferably provided with externally recognisable markings by means of which the operator can see their respective function.

It is therefore clear that a dental handpiece set constructed according to the invention has considerable practical advantages. The operator can select freely and irrespective of the power supply component available the tools he requires for dental treatment and also the advantageous working speeds for the treatment. He merely needs a coupling adapter suitable for the available supply component. Subsequently, he is able to assemble and also to fit together in a simple manner, the arrangement of the dental handpiece apparatus required in each case, if necessary with the interposition of an intermediate piece 101. This means that it is not necessary to have an integral, complete dental handpiece for each type of work; the handpiece can on the contrary be assembled as required from individual components.

This is of considerable advantage on the one hand when different methods of treatment and treatment tools are required on isolated occasions.

However, the invention is also of advantage if different power supply components are available, for example for peripatetic dental treatment in large supply areas, such as in developing countries for example where different supply components are available in the various places where dental treatment is given. It is then no longer necessary to have complete dental handpieces suitable for each power supply component. It is sufficient merely to provide suitable coupling adapters.

Therefore, in such circumstances the purchasing costs are considerably reduced.

In addition a compact design and good handling by the operator are ensured.

The embodiments described above with reference to the drawings are preferred arrangements of dental handpiece sets, but many other constructions may be provided, if desired, within the scope of the present invention.

I claim:

1. A dental handpiece set comprising a handpiece housing, a power supply module detachably coupled to one end of the handpiece housing for supplying power to operate the handpiece, means provided in the handpiece housing to mount therein a motor unit which is coupled to the power supply module, and a drive train extending within the handpiece housing to an opposite end of the handpiece housing at which a dental implement can be mounted to be driven by the drive train when the motor used is mounted in the handpiece housing:

in which said one end of the handpiece housing is adapted removably to receive the motor unit, as an exchangeable motor unit, so that a housing of the motor unit is securable against rotation within the handpiece housing;

and in which at least two functionally different types of motor units are provided to be mounted selectively in the handpiece housing according to operation requirements for the dental handpiece, each motor unit being arranged so as to be capable of being received by the handpiece housing via said one end thereof and being adapted for coupling with the power supply module.

2. A dental handpiece set according to claim 1, comprising a dental-implement-mounting portion and a motor-mounting portion which are connected together to form said handpiece housing;

in which the motor-mounting portion is arranged at its end facing said power supply module to receive therein the selected motor unit, and at its opposite end is arranged to receive a gear drive unit which is operable to transmit drive from the motor unit to said drive train;

and in which at least two different gear drive units are provided to be mounted selectively in said opposite end of the motor-mounting portions according to operating requirements of the handpiece, said gear drive units having different transmission ratios.

3. A dental handpiece set according to claim 1, in which at least one of said motor units is a fluid-operated motor, and said power supply module includes a fluid supply line and is arranged to deliver a supply of compressed fluid to said fluid-operated motor.

4. A dental handpiece set according to claim 1, in which at least one of said motor units is an electric motor, and said power supply module includes an electrical supply line and is arranged to supply electrical power to operate the electric motor.

5. A dental handpiece set according to claim 1, in which at least one of said motor units is integrated with a respective power supply module to form a unitary construction therewith.

6. A dental handpiece set according to claim 1, including a coupling adapter which is insertable in said handpiece housing to be located non-rotatably therein and intermediate the selected motor unit and said power supply module, the coupling adapter being adapted to be coupled with the power supply module in a secure but detachable manner which permits relative rotation therebetween.

7. A dental handpiece set according to claim 2, in which said opposite end of the motor-mounting portion and an output of each of said gear drive units are arranged so that at least two different implement-mounting portions can be connected thereto.

8. A dental handpiece set according to claim 1, in which said power supply module includes a plurality of different supply lines, and said handpiece housing and/or each motor unit includes connections for each of said plurality of different supply lines.

9. A dental handpiece set according to claim 6, in which said power supply module includes a plurality of different supply lines, and said coupling adapter has connections at its end facing the power supply module to correspond with respective different supply lines of the power supply module, and at its opposite end the coupling adapter has the same arrangement for the motor unit and the handpiece housing in respect of all power supply modules to be used with the handpiece set.

10. A dental handpiece set according to claim 6, in which said power supply module includes a plurality of different supply lines and including an intermediate part which is insertable in said handpiece housing to be located non-rotatably between the selected motor unit and said coupling adapter said intermediate part having connections corresponding to each of the plurality of different supply lines of the power supply module such that, at the motor-end of the intermediate part, there is the same arrangement in respect of the motor unit and the handpiece housing for all power supply modules to be used with the handpiece set.

11. A dental handpiece set according to claim 6, including a signal converter associated with the coupling adapter and comprising a signal emitter component and a signal receiver component, with one of said components being connected to said power supply module.

12. A dental handpiece set according to claim 11, in which the signal emitter component comprises a light source arranged at the motor-end of the power supply module, and the signal receiver component comprises a light receiver.

13. A dental handpiece set according to claim 12, in which the light receiver comprises an end face of a fibre optic light guide.

14. A dental handpiece set according to claim 3, in which said motor unit is a rotary vane type motor.

15. A dental handpiece set according to claim 1, in which said motor units have substantially the same external dimensions, at least at the entry end of the units to the handpiece housing.

16. A dental handpiece set according to claim 2, in which said gear drive units have substantially the same external dimensions.

17. A dental handpiece set according to claim 1, including a snap-action coupling for the power supply module.

18. A dental handpiece set according to claim 2, including a snap-action coupling for joining together the portions of the handpiece housing.

19. A dental handpiece set according to claim 2, including at least one coupling adapter which is insertable in said handpiece housing to be located non-rotatably therein and intermediate the selected motor unit and said power supply module, in which the motor-mounting portion of the handpiece housing is in two parts comprising a first part which receives the selected motor unit and a second part which receives the coupling adapter, said first and second parts being connectible together with their adjacent faces in a predetermined angular position with respect to each other.

* * * * *